United States Patent [19]

Takase

[11] Patent Number: 4,920,968

[45] Date of Patent: May 1, 1990

[54] NEEDLE BASE WITH PLURAL NEEDLES FOR SUBCUTANEOUSLY APPLYING ELECTRIC CURRENT

[76] Inventor: Haruo Takase, 20-16,3-chome, Shimoochiai Shinjuku-ku, Tokyo, Japan

[21] Appl. No.: 332,401

[22] Filed: Mar. 28, 1989

Related U.S. Application Data

[63] Continuation of Ser. No. 142,787, Jan. 11, 1988, abandoned.

[30] Foreign Application Priority Data

Jan. 20, 1987 [JP]  Japan ................................ 62-6395[U]

[51] Int. Cl.⁵ ............................................... A61B 5/04
[52] U.S. Cl. ................................... 128/639; 128/799; 606/36
[58] Field of Search ............... 128/783, 784, 799, 800, 128/802, 639–644, 303.14, 303.19

[56] References Cited

U.S. PATENT DOCUMENTS

| | | | |
|---|---|---|---|
| 1,445,961 | 2/1923 | Kree | 128/303.18 |
| 1,532,462 | 4/1925 | Winterfield | 128/799 |
| 1,906,802 | 5/1933 | Miller | 128/784 |
| 2,023,563 | 12/1935 | Willison | 128/784 |
| 2,238,344 | 4/1941 | Schuler et al. | 128/784 |
| 3,035,580 | 5/1962 | Guiorguiev | 128/303.18 |
| 3,670,736 | 6/1972 | Panico | 128/800 |
| 4,034,762 | 7/1977 | Cosens et al. | 128/303.17 |
| 4,233,987 | 11/1980 | Feingold | 128/639 |
| 4,685,466 | 8/1987 | Rau | 128/640 |

FOREIGN PATENT DOCUMENTS 243478  4/1945  Switzerland ................ 128/303.18

*Primary Examiner*—Max Hindenburg
*Assistant Examiner*—J. P. Lacyk
*Attorney, Agent, or Firm*—Frishauf, Holtz, Goodman & Woodward

[57] ABSTRACT

A needle base device for subcutaneously supplying electric current which simplifies surgical procedures and which saves time for plastic surgery such as hair removal by cauterization and/or coagulation of hair follicles, subcutaneous adipose tissues and/or sebaceous glands comprises a non-conductive plate-like member and a large number of conductive needles which are implanted on the plate-like member at a predetermined interval or spacing. The needles project from the plate-like member in substantially the same direction substantially in parallel to each other with the bottom thereof embedded in the plate-like member. The needles are conductively connected to each other to thereby allow simultaneous application of electric current thereto.

10 Claims, 2 Drawing Sheets

FIG_1
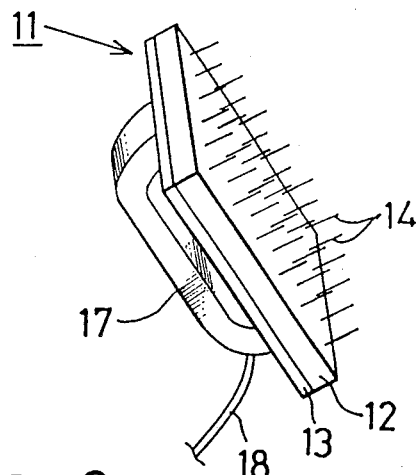
FIG_2
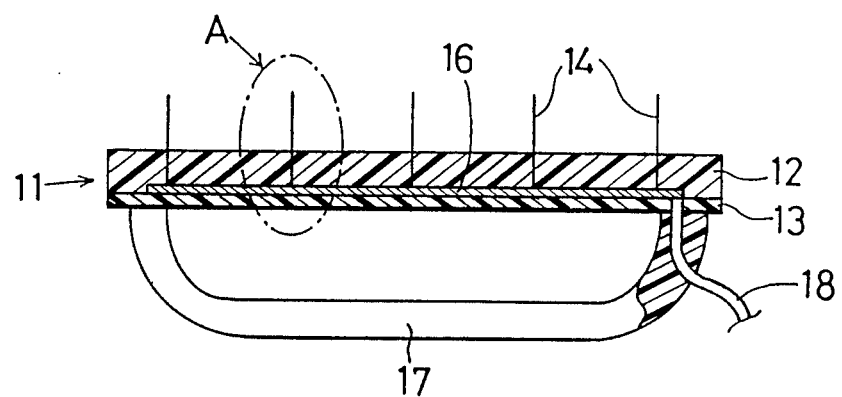
FIG_3
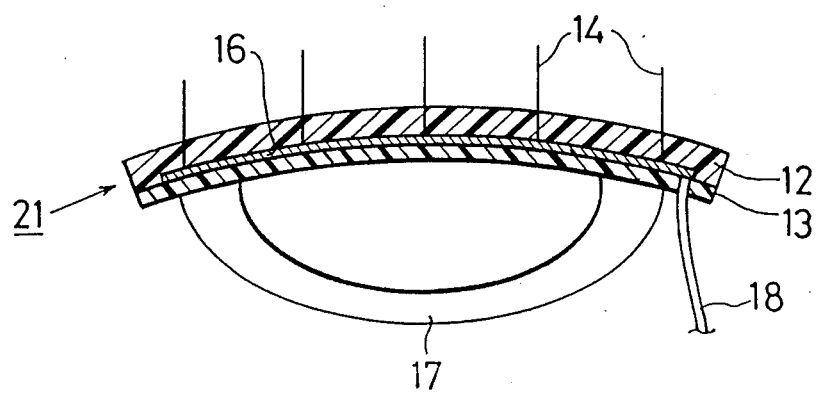

FIG_ 4
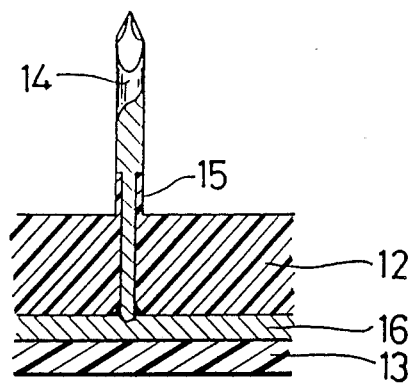
FIG_ 5
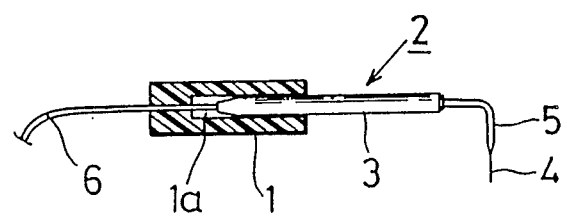

NEEDLE BASE WITH PLURAL NEEDLES FOR SUBCUTANEOUSLY APPLYING ELECTRIC CURRENT

This application is a continuation of application Ser. No. 07/142,787, filed Jan. 11, 1988 now abandoned.

FIELD OF INVENTION

This invention relates to a base plate for needles used for subcutaneously applying electric current in plastic surgery, and more particularly to a needle base which is implanted with a large number of needles at predetermined intervals on one surface of a substrate for passing electric current and which connects all the needles conductively on the bottoms thereof so as to enable simultaneous application of predetermined electric current on these needles.

BACKGROUND OF THE INVENTION

In the prior art, individual needles shown in FIG. 5 have been used to apply subcutaneously electric current for cauterization and/or coagulation of hair follicles, subcutaneous adipose tissues or sebaceous glands in order to remove hair in plastic surgery. Such a needle comprises a jig 1 made of synthetic resin and an attachment needle member 2 which is to be inserted into a hole 1a of the jig 1. The attachment needle member 2 comprises an electrode 3, a needle 4 which is bent at a substantially right angle from the end of said electrode, and a non-conductive member 5 made of synthetic resin or other material which is placed over said needle 4 on the exposed part thereof extending from the electrode 3 except for a tip end which is to be inserted into the skin. A wire 6 is connected to the jig 1 at the rear end thereof so as to reach the electrode 3. In practice, the jig 1 is held with fingers to position the end of a needle 4 in a pore on the skin at a surgery site, and pushed down into the skin to a predetermined depth until the end of said non-conductive member 5 abuts on the skin, and then predetermined electric current is supplied to perform such surgery operations as cauterization, coagulation, etc. of hair follicles, subcutaneous adipose tissues or sebaceous glands.

When used for plastic surgery, it is necessary to prick the skin by plural sets of the jig 1 and the attachment needle member 2 in a pattern parallel to each other but with an interval of generally 3–5 mm, and to supply the predetermined electric current to all of the needles respectively. The operation therefore needs considerable skill and experience as well as cumbersome manual operations. Heretofore, much skill and experience was required to arrange a large number of needles separately at an interval but in parallel and in the same direction, insert them in that arrangement under the skin, and supply electric current separately to individual needles. Moreover, the prior art needles tend to apply electric current on the upper surface cuticles in addition to the surgery site penetrated with the needles to thereby inconveniently affect and damage the skin surface by cauterization.

SUMMARY OF THE INVENTION

An object of this invention is to provide a needle base for passing electric current subcutaneously, and which can insert a large number of needles under the skin simultaneously and which can supply electric current to all the needles simultaneously to thereby remarkably shorten the operating time as well as to simplify the surgery.

Another object of this invention is to provide a needle base which can precisely specify a subcutaneous site to apply the electric current by inserting a large number of needles which are arranged in a position parallel to each other at an interval to thereby simplify the surgery procedure.

Still another object of this invention is to provide a needle base for subcutaneously supplying electric current in plastic surgery which can insert a large number of needles to a uniform subcutaneous depth even on resilient locations such as the abdomen. In order to achieve such objects, the needle base of the present invention comprises a non-conductive substrate, and a large number of needles which are implanted on a side surface of the substrate at a predetermined interval and which are electrically connected to each other on their bottom portions.

BRIEF DESCRIPTION OF THE DRAWINGS

FIG. 1 is a perspective view of an embodiment of a needle base of present invention for subcutaneous electric current supply used in plastic surgery.

FIG. 2 is a cross sectional view to partially show the embodiment shown in FIG. 1 in enlargement.

FIG. 3 is a partial cross section to show another embodiment of a needle base of the present invention in enlargement.

FIG. 4 is an enlarged view of the portion encircled by the letter A in FIG. 2.

FIG. 5 is a cross sectional view to show a part of a prior art needle for subcutaneously supplying electric current.

DETAILED DESCRIPTION

This invention relates to a needle base for subcutaneously supplying electric current which can be easily used in various types of plastic surgery without requiring surgical expertise and yet which is effective for such purposes as cauterization of hair follicles and/or cauterization or coagulation of sebaceous glands to remove hair, etc. The invention will now be described in more detail, referring to the most preferred embodiments shown in FIGS. 1 through 4.

As shown in FIGS. 1, 2, and 4, an insulating substrate or base 11 has a large number of electrically conductive (preferably metal) needles 14 embedded therein and projecting from one side of said substrate 11. The needles 14 are arranged with a predetermined interval or spacing therebetween (for example, 5 mm). The needles 14 are used for subcutaneously supplying electric current.

The base or substrate 11 comprises a laminated structure which includes a main plate member 12 and a cover plate member 13. The main plate member 12 and cover plate member 13 are both made of insulating material such as plastics. As shown in FIG. 4, on the insulating main plate 12 are provided the needles 14 for subcutaneously supplying electric current with their bottoms embedded at an interval (i.e. spaced from each other) and with their tip ends projected from one surface of the plate 12, each needle being partially covered with a non-conductive covering member 15 made of plastics or other materials in a manner to have the same diameter on the covered portion as on the exposed portion. To this end, the needles 14 have a necked down or reduced diameter portion to receive non-conductive covering member 15. The other surface of the main plate 12 is wired (for example by printed circuit techniques) with a conductive member 16 in a grid pattern aligned with the pattern of said needles 14. Needles 14 are electrically connected to conductive member 16. The cover plate 13 made of an insulating material such as plastics is integrally laminated over the whole surface of the other surface of the main plate 12 via an appropriate adhesive agent. The numeral 17 denotes a handle (preferably made of insulating material) attached on the substrate 11, and 18 an electric cord or wire which is electrically connected to a part of said conductive member 16 to supply electrical current to conductive member 16 and to the needles 14.

FIG. 3 shows another embodiment of this invention. The structure of the second embodiment is similar to that of the first embodiment except for that a substrate 21 implanted with the needles 14 is convex so as to have the highest point at the center thereof.

In plastic surgery, after administrating local anesthesia on the specified site and disinfecting the site with alcohol, etc., the handle 17 is held by a hand to tightly press the surface which is implanted with a large number of needles 14 on the skin and to push the needles 14 into the skin.

A predetermined electric current is then supplied to the conductive member 16 inside the substrate 11 via the electric cord or wire 18 to apply to the skin at a predetermined depth the desired degree of electric current via the needles 14 in the order generally used for coagulation to achieve coagulation of sebaceous glands, coagulation or cauterization of hair follicles or other plastic surgery.

As described in detail in the foregoing, the needle base of the present invention can subcutaneously insert a large number of needles simultaneously at an appropriate interval or spacing to a predetermined depth in the skin in precise positional relation without requiring considerable skill and complex manual operations which heretofore were needed to achieve the same effect, since the needles are pre-implanted in a large number at the predetermined desired spacing or interval on one surface of a substrate and are conductively connected to each other via conductive member 16.

The needle base device of the present invention further can save time needed for surgery to a remarkable extent as the base can supply electric current to all the needles simultaneously, unlike the prior art base which feeds electric current separately to individual needles. If the substrate is made convex to increase the height of the needles at the center thereof as shown in the second embodiment of FIG. 3, the needles implanted at or near the center can be inserted to a relatively deeper depth in the skin to thereby enable insertion of the needles evenly into the skin even if the site is curved.

As the lower portion near the bottom of a needle is coated with a non-conductive member 15 to a predetermined height according to this invention, the skin will not be affected by cauterization at all except for the desired sites and at the predetermined depth. The needle base device of the present invention is advantageous, moreover, in that coagulation and cauterization can be performed at a large number of locations simultaneously.

While the needles 14 are described as projecting by the same amount from the substrate 11 (FIG. 1) and 21 (FIG. 3), they could be arranged to project by predetermined different amounts, as desired or required for a given operation.

We claim:

1. A needle base device for subcutaneously supplying electric current to the skin of a patient, comprising:
   a non-conductive member having a plurality of conductive needles mounted thereon for piercing a skin portion of the patient, said needles projecting from an outer surface of said non-conductive member;
   said non-conductive member comprising a convex plate-like member which protrudes outward toward the free ends of said needles at the central portion of said plate-like member, and said needles each perpendicularly projecting from said non-conductive plate-like member by substantially the same amount whereby more efficient and uniform cauterization is facilitated;
   said needles each having bottom ends embedded in said non-conductive member and being spaced from one another both laterally and horizontally by predetermined equal intervals or spacings, said needles having respective free ends opposite said embedded bottom ends;
   said needles each having a non-conductive covering over a portion of the length thereof which projects from said non-conductive member, said non-conductive covering extending from said non-conductive member to a portion of said respective needles intermediate the free and bottom ends thereof, said needles being uncovered over the remainder of their lengths between said intermediate portion and said free end thereof, the outer diameter of said non-conductive covering being the same as the outer diameter of the uncovered portions of said needles between said intermediate portions and said free ends thereof; and
   conductive means coupled to said non-conductive member and to said bottom ends of said needles for conductively connecting together said bottom ends of said needles for simultaneously supplying electrical energy to a plurality of said needles so as to enable simultaneous application of predetermined electric current to at least said plurality of said needles.

2. The needle base device of claim 1, wherein said non-conductive member comprises a main plate member and a cover plate member, said main plate member having said bottom ends of said needles embedded therein and said needles projecting from one surface thereof, said conductive means being coupled to said bottom ends of said needles at another surface of said main plate member which is opposite to said one surface from which said needles project, and wherein said cover plate member is secured to said another surface of said main plate member to cover said conductive means.

3. The needle base device of claim 2, wherein said conductive means comprises a convex plate-like conductive member electrically coupled to said bottom ends of said needles.

4. The needle base device of claim 2, further comprising a handle member coupled to said non-conductive member for facilitating handling of said needle base device.

5. The needle base device of claim 4, wherein said handle member projects from said main plate member in a direction opposite to the direction said needles project therefrom, and is integrally coupled with said cover plate member.

6. The needle base device of claim 1 wherein said non-conductive covering on said needles is integrally formed with said non-conductive member, and projects from said non-conductive member along a given length of said needles.

7. The needle base device of claim 1, wherein said non-conductive covering covers a substantial portion of the length of said needles.

8. The needle base device of claim 1, wherein each of said needles comprises an elongated metallic rod-like member, said elongated metallic rod-like member having a reduced diameter portion adjacent said non-conductive member and extending from said non-conductive member; and said non-conductive covering covers said reduced diameter portion and has an outer diameter which is the same as the outer diameter of the portion of said rod-like elongated member which is not of said reduced diameter.

9. The needle base device of claim 1, wherein said needles are arranged in a plurality of vertical and lateral rows so as to form a matrix-type array of said needles over a substantially large area.

10. The needle base device of claim 9, wherein said needles are substantially equidistantly spaced from each other.

* * * * *